_United States Patent_ [19]

Porter et al.

[11] Patent Number: 4,938,966
[45] Date of Patent: Jul. 3, 1990

[54] CONTROLLED RELEASE FLECAINIDE ACETATE FORMULATION

[75] Inventors: David Porter; Andrew M. Twitchell, both of Loughborough, United Kingdom

[73] Assignee: Riker Laboratories, Inc., St. Paul, Minn.

[21] Appl. No.: 277,899

[22] Filed: Nov. 30, 1988

[51] Int. Cl.$^5$ .................................................. A61K 9/62
[52] U.S. Cl. ...................................... 424/456; 424/78; 424/462; 424/497
[58] Field of Search ................. 424/497, 78, 462, 456, 424/499

[56] References Cited

U.S. PATENT DOCUMENTS

| | | | |
|---|---|---|---|
| 3,900,481 | 8/1975 | Banitt et al. ..................... | 424/274 X |
| 4,098,890 | 7/1978 | Molloy .......................... | 424/248.4 X |
| 4,285,955 | 8/1981 | Wehinger et al. .............. | 514/821 X |
| 4,604,394 | 8/1986 | Kaczorowski et al. ........... | 514/255 |

_Primary Examiner_—Thurman K. Page
_Attorney, Agent, or Firm_—Donald M. Sell; Walter N. Kirn; Robert W. Sprague

[57] ABSTRACT

Controlled release pharmaceutical formulations containing flecainide acetate and methods of suppressing arrhythmia using the formulations are described.

10 Claims, No Drawings

CONTROLLED RELEASE FLECAINIDE ACETATE FORMULATION

TECHNICAL FIELD

This invention relates to flecainide acetate controlled release formulations, capsules containing such formulations and pharmacological methods for using such formulations.

BACKGROUND OF THE INVENTION

Flecainide acetate (commercially available from Riker Laboratories, Inc. under the trade designation Tambocor ® brand flecainide acetate) is an antiarrhythmic agent that is clinically effective for the suppression of ventricular arrhythmias. Conventional release flecainide acetate tablets must generally be administered twice daily to maintain effective plasma levels.

BRIEF DESCRIPTION OF THE INVENTION

The present invention provides a novel flecainide acetate controlled release pharmaceutical formulation comprising a film-coated bead. The bead is comprised of from about 20 to 80 percent by weight based on the total weight of the bead of flecainide acetate and about 80 to 20 percent by weight of microcrystalline cellulose. The film-coat is comprised of from about 40 to 70 percent by weight based on the total weight of the film-coat of a methacrylic acid/methyl methacrylate copolymer, about 5 to 20 percent by weight of a plasticizer and about 20 to 50 percent by weight of a lubricant. The film-coat is generally present in an amount of about 5 to 20 percent by weight based on the total weight of the film-coated bead.

The present invention also provides a flecainide acetate capsule exhibiting a controlled release of flecainide acetate in a human digestive tract. The flecainide acetate controlled release formulations of the present invention allow for once-a-day administration which will promote better patient compliance. The formulations also provide lower peak plasma levels than conventional release tablets which may mimimize the incidence of side effects. The formulations provide controlled release of flecainide acetate over a broad pH range that may be encountered in the digestive tract.

DETAILED DESCRIPTION OF THE INVENTION

The flecainide acetate controlled release pharmaceutical formulations of the present invention comprise a film-coated bead which comprises a bead coated with a film-coat.

The bead is generally comprised of from about 20 to 80 percent, preferably about 70 to 80 percent, and most preferably about 75 percent, by weight based on the total weight of the bead of flecainide acetate and from about 80 to 20 percent, preferably about 20 to 30 percent, and most preferably about 25 percent, by weight of microcrystalline cellulose. Flecainide acetate may be prepared using the method disclosed in U.S. Pat. No. 3,900,481 or that disclosed in U.S. Pat. No. 4,642,384, both incorporated herein by reference. A preferred microcrystalline cellulose is Avicel TM pH101. The bead is prepared by granulating a mixture of flecainide acetate and microcrystalline cellulose using water as a granulating liquid. It is currently preferred that the flecainide acetate be milled through a 40 mesh screen and th microcrystalline cellulose be sifted through a 500 micrometer sieve prior to granulation. The granulate is then put through an extruder head and the extrudate is in turn placed in a spheroniser. The resulting spheres are dried until they have a moisture content of approximately 1% by weight. The dried spheres are sifted to remove both oversize beads and fines.

The film-coat of the invention is comprised of from about 40 to 70 percent, preferably about 57 percent, by weight based on the total weight of the film-coat of a methacrylic acid/methyl methacrylate copolymer, about 5 to 20 percent, preferably about 10 percent, by weight of a plasticizer and about 20 to 50 percent, preferably about 33 percent, by weight of a lubricant. The preferred copolymer is USP/NF methacrylic acid copolymer Type B available from Rohm Pharma as Eudragit TM S100. The plasticizer is preferably selected from the group consisting of polyethylene glycols, dibutyl phthalate and citric acid esters. Currently polyethylene glycol 400 is the preferred plasticizer. The lubricant serves to decrease the tendency of the beads to agglomerate and to produce more uniform surfaces. Any pharmaceutically acceptable lubricant which does not adversely interact with the copolymer or with the flecainide acetate may be used. Currently talc is the preferred lubricant. A suspension suitable for film-coating the beads is generally prepared by dispersing first the plasticizer and then the lubricant in a solution of the copolymer in a mixture of water and ethanol. The film-coating suspension is applied to the beads using a conventional fluidized-bed system such as Strea-2. The film-coat will generally be present in an amount of about 5 to 20 percent, preferably about 9 percent, by weight based on the total weight of the film-coated bead. The film-coated beads are passed through a 1600 micrometer sieve to remove any agglomerates.

The film-coated beads of the invention are filled into capsule shells using conventional capsule-filling equipment. The capsule shell used should be soluble in gastrointestinal fluid. The preferred capsule shells are hard gelatin capsules.

The preferred embodiment of this invention is described by way of Example.

Example 1 Part A

Preparation of Uncoated Bead

Sixty (60) kg of flecainide acetate was milled through a 40 mesh wire-woven screen at high speed using an Apex comminuting mill. 6.67 kg of microcrystalline cellulose EP/NF (Avicel TM grade pH101, commercially available from FMC Corporation was sifted through a 500 micrometer screen of a Russell sieve. The sieved microcrystalline cellulose was blended with 20.00 kg of the milled flecainide acetate for 10 minutes using a planetary mixer at speed one. 11.20 kg of purified water was added with mixing over a period of 5 minutes. Mixing was continued for 2 minutes after the addition. The mixer was stopped, the sides of the mixer bowl were scraped and then mixing was continued until a uniform granulate was obtained. The granulate was passed through a NICA extruder using an extruder head speed of 100 rpm, a feeder paddle speed of 100 rpm and a 1 mm extrusion screen. Approximately 13 kg portions of the extrudate were placed in a Calvea spheroniser at 300–325 rpm for 10 minutes. The resulting spheres were dried in approximately 20 kg batches in a Strea-2 fluidized bed drier (available from Aeromatic using an inlet temperature of 50° C. and a fluidizing air volume flow rate of 450–500 m³/hr until a moisture content of approximately 1% w/w (loss on drying 2 hours at 60° C. with vacuum) was obtained. The dried spheres were sifted through a 1250 micrometer sieve to remove oversize material and through a 500 micrometer sieve to remove fines.

Part B
Film Coating of Beads

A solution of Eudragit TM S100 (methacrylic acid copolymer, type B USP) was prepared by slowly dispersing 1.496 kg of Eudragit TM S100 powder in a mixture of 7.744 kg purified water and 11.616 kg ethanol while stirring with a motorized paddle. The dispersion was covered and stirring was continued for about 1 to 2 hours until the majority of the Eudragit TM S100 had hydrated and dissolved. The dispersion was allowed to stand covered overnight to provide a clear colorless solution. The weight was checked and additional solvent mixture was added if necessary followed by 5 minutes of stirring. 0.264 kg of polyethylene glycol 400 USP was dispersed into the Eudragit TM S100 solution and the resulting mixture stirred for 5 minutes. Then 0.880 kg of talc EP/USP was added and the resulting suspension was stirred for 15 minutes. 25.00 kg of uncoated beads, prepared in accordance with Part A, were placed in the bowl of a Strea-2 fluidized bed drier. The coating conditions were as follows: temperature setting 45–50° C., peristaltic pump, nozzle size 1.2 mm, atomising air pressure 3.5 bar and air volume 350 to 400 m³. When the inlet temperature reached 50° C. and the exhaust temperature was approximately 30° C., the peristaltic pump was turned on. The inlet air temperature setting was adjusted as necessary to maintain the outlet air temperature at approximately 30° C. The coating process was continued until 20.313 kg of coating suspension had been applied. The weight of the coated beads was 27.088 kg. The coated beads were passed through a 1600 micrometer sieve to remove any agglomerates.

Part C
Encapsulation

Hard gelatin capsule shells were filled with coated beads prepared in accordance to Part B. The unit dose quantity of each ingredient is shown in Table 1.

TABLE 1

| Ingredient | mg per capsule |
| --- | --- |
| Flecainide Acetate | 200.00 |
| Microcrystalline cellulose | 66.67 |
| Talc | 8.66 |
| Eudragit TM S100 | 14.74 |
| Polyethylene glycol 400 | 2.60 |

The following relates to studies involving capsules of the invention prepared essentially according to Example 1 except that procedures were on a smaller scale (i.e., 0.5 kg scale).

The capsules of the invention and a commercially available conventional release tablet containing 200 mg of flecainide acetate intended to be dosed every twelve hours were administered orally in a single dose cross over study with a wash-out period of 5 to 7 days to nine fasted human subjects. The concentration of unchanged flecainide acetate in plasma was measured by use of a sensitive and selective liquid chromatographic method based on the method described by S. F. Chang, A. M. Miller. J. M. Fox and T. M. Welscher, Therapeutic Drug Monitoring, 6:105–111 (1984), Raven Press, New York, incorporated herein by reference. Prior to chromatographic analysis, flecainide acetate and the added internal standard were separated from plasma by use of an octyl ($C_8$) extraction column with a series of washings and a methanol elution. The eluant containing the flecainide acetate and the added internal standard was chromatographed and detected using a Waters HPLC system with Shimadzu fluorescence detector. Single aliquots (1.0 ml or 0.5 ml) of plasma samples were analyzed. The range of the calibration curve was from 25 to 600 ng/ml. However, samples with flecainide acetate concentrations less than 25 ng/ml were reanalyzed using a calibration curve that ranged from 12.5 to 300 ng/ml. Ten percent of the samples were randomly selected on a daily basis for repeat analysis to monitor the precision of the method. All replicate values for a given sample were averaged, with the average used in pharmacokinetic calculations. Analytical results reported as below the standard curve were not used in any mean plasma level calculations; they were used, however, in the median determination. Analytical reference samples were routinely carried through the extraction and chromatographic procedures in parallel with each group of unknown plasma samples. Reference samples between 12.5 and 600 ng flecainide acetate per milliliter were prepared by adding known amounts of flecainide acetate to blank human plasma; thus, plasma levels of the flecainide acetate are expressed as ng/ml of flecainide acetate. For each sample set, relative peak height responses (flecainide acetate/internal standard) were related to flecainide acetate concentrations in analytical reference samples using linear regression analysis; the slope and intercept from the least squares line were used to determine flecainide acetate concentrations in the unknown samples. Results were as follows:

Table 2 shows the plasma flecainide acetate concentrations following the oral administration of two 100 mg conventional-release tablet. Table 3 shows the plasma flecainide acetate concentrations following the oral administration of a single 200 mg capsule of the invention. Table 4 shows peak levels and time to peak plasma flecainide acetate levels in nine fasted subjects following the oral administration of two 100 mg conventional release tablets and of a 200 mg capsule of the invention.

As can be seen from the results in Tables 2, 3 and 4 above, the formulation of the invention provides a controlled release of flecainide acetate resulting in lower peak plasma levels and a longer half-life when compared to commercially available conventional release tablets intended for dosing every twelve hours.

TABLE 2

PLASMA FLECAINIDE ACETATE CONCENTRATIONS IN NINE FASTED SUBJECTS
FOLLOWING A SINGLE 200 mg ORAL DOSE OF THE CONVENTIONAL-RELEASE TABLET

| | | Concentration (ng/mL) at Hours Postdose | | | | | | | | | | | | | | | | | |
| --- | --- | --- | --- | --- | --- | --- | --- | --- | --- | --- | --- | --- | --- | --- | --- | --- | --- | --- | --- |
| Subj | Predose | 0.5 | 1 | 1.5 | 2 | 3 | 4 | 6 | 8 | 10 | 13 | 16 | 22 | 26 | 30 | 34 | 40 | 48 | 58 |
| 1 | 0 | 33 | 177 | 270 | 262 | 275 | 272 | 259 | 203 | 184 | 163 | 128 | 97 | 77 | 67 | 57 | 41 | 26 | 19 |
| 2 | 0 | 0 | 32 | 121 | 131 | 215 | 250 | 246 | 215 | 191 | 153 | 122 | 87 | 67 | 53 | 42 | 26 | 16 | a |

TABLE 2-continued
PLASMA FLECAINIDE ACETATE CONCENTRATIONS IN NINE FASTED SUBJECTS FOLLOWING A SINGLE 200 mg ORAL DOSE OF THE CONVENTIONAL-RELEASE TABLET

| Subj | Predose | 0.5 | 1 | 1.5 | 2 | 3 | 4 | 6 | 8 | 10 | 13 | 16 | 22 | 26 | 30 | 34 | 40 | 48 | 58 |
|---|---|---|---|---|---|---|---|---|---|---|---|---|---|---|---|---|---|---|---|
| 3 | 0 | 16 | 135 | 185 | 225 | 284 | 272 | 273 | 221 | 192 | 156 | 118 | 83 | 63 | 51 | 37 | 23 | 14 | a |
| 4 | 0 | 27 | 171 | 276 | 308 | 339 | 305 | 284 | 238 | 204 | 184 | 156 | 110 | 98 | 88 | 63 | 41 | 29 | 19 |
| 5 | 0 | 100 | 244 | 275 | 315 | 340 | 336 | 312 | 266 | 220 | 168 | 144 | 99 | 79 | 66 | 50 | 20 | 20 | 13 |
| 6 | 0 | 33 | 150 | 242 | 286 | 300 | 305 | 294 | 281 | 245 | 209 | 171 | 128 | 95 | 83 | 66 | 50 | 33 | 22 |
| 7 | 0 | 53 | 161 | 275 | 278 | 351 | 319 | 347 | 302 | 270 | 233 | 187 | 128 | 113 | 95 | 71 | 52 | 32 | 22 |
| 8 | 0 | 131 | 303 | 334 | 340 | 330 | 303 | 298 | 249 | 209 | 187 | 147 | 98 | 81 | 71 | 50 | 31 | 21 | 0 |
| 10 | 0 | 18 | 135 | 271 | 292 | 323 | 332 | 345 | 301 | 244 | 236 | 210 | 147 | 117 | 102 | 76 | 57 | 37 | 22 |
| Median | 0 | 33 | 161 | 271 | 286 | 323 | 305 | 294 | 249 | 209 | 184 | 147 | 99 | 81 | 72 | 57 | 41 | 26 | 19 |
| Mean | 0 | 45.7 | 168 | 250 | 271 | 306 | 299 | 295 | 253 | 218 | 188 | 154 | 109 | 87.8 | 75.2 | 56.9 | 38.9 | 25.3 | 16.7 |
| S.D. | 0 | 42.8 | 75.1 | 62.0 | 61.8 | 43.2 | 29.2 | 35.0 | 36.9 | 29.5 | 31.7 | 30.9 | 21.5 | 19.1 | 17.9 | 13.2 | 12.3 | 8.0 | 8.0 |
| n | 9 | 9 | 9 | 9 | 9 | 9 | 9 | 9 | 9 | 9 | 9 | 9 | 9 | 9 | 9 | 9 | 9 | 9 | 7 | a: Value is below 12.5 ng/mL.

TABLE 3
PLASMA FLECAINIDE ACETATE CONCENTRATIONS IN NINE FASTED SUBJECTS FOLLOWING A SINGLE 200 mg ORAL DOSE OF A CAPSULE OF THE INVENTION

| Subj | Predose | 0.5 | 1 | 1.5 | 2 | 3 | 4 | 6 | 8 | 10 | 13 | 16 | 22 | 26 | 30 | 34 | 40 | 48 | 58 |
|---|---|---|---|---|---|---|---|---|---|---|---|---|---|---|---|---|---|---|---|
| 1 | 0 | 0 | 0 | 0 | a | 14 | 22 | 44 | 60 | 73 | 83 | 95 | 120 | 130 | 136 | 123 | 96 | 68 | 46 |
| 2 | 0 | 0 | 0 | 0 | a | a | 14 | 39 | 54 | 74 | 102 | 100 | 95 | 94 | 82 | 68 | 43 | 25 | 16 |
| 3 | 0 | 0 | 0 | a | a | 16 | 25 | 55 | 64 | 79 | 107 | 124 | 116 | 110 | 102 | 82 | 59 | 33 | 18 |
| 4 | 0 | 0 | 0 | a | 16 | 29 | 58 | 81 | 99 | 122 | 119 | 110 | 89 | 76 | 66 | 54 | 37 | 24 | 15 |
| 5 | 0 | 0 | 0 | a | a | 27 | 33 | 67 | 82 | 105 | 157 | 175 | 159 | 160 | 132 | 110 | 73 | 44 | 28 |
| 6 | 0 | 0 | 0 | 0 | a | 18 | 26 | 64 | 91 | 100 | 112 | 131 | 141 | 154 | 150 | 134 | 106 | 77 | 52 |
| 7 | 0 | 0 | 0 | a | a | 19 | 26 | 50 | 92 | 114 | 133 | 155 | 147 | 166 | 170 | 148 | 100 | 65 | 40 |
| 8 | 0 | 0 | 0 | a | 15 | 23 | 24 | 50 | 60 | 71 | 82 | 106 | 114 | 126 | 122 | 103 | 56 | 38 | 25 |
| 10 | 0 | 0 | a | a | 15 | 26 | 38 | 72 | 85 | 121 | 174 | 184 | 158 | 147 | 123 | 92 | 65 | 52 | 25 |
| Median | 0 | 0 | 0 | a | a | 19 | 26 | 55 | 82 | 100 | 112 | 124 | 120 | 130 | 123 | 103 | 65 | 44 | 25 |
| Mean | 0 | 0 | 0 | 0 | 15.3 | 21.5 | 29.6 | 58.0 | 76.3 | 95.4 | 119 | 131 | 127 | 129 | 120 | 102 | 70.6 | 47.3 | 29.4 |
| S.D. | 0 | 0 | 0 | 0 | 0.6 | 5.5 | 12.6 | 13.9 | 16.8 | 21.3 | 31.2 | 33.0 | 25.9 | 31.0 | 32.6 | 30.8 | 25.1 | 19.3 | 13.5 |
| n | 9 | 9 | 9 | 8 | 4 | 3 | 8 | 9 | 9 | 9 | 9 | 9 | 9 | 9 | 9 | 9 | 9 | 9 | 9 | a: Value is below 12.5 ng/mL.

TABLE 4
PEAK LEVELS AND TIME TO PEAK PLASMA FLECAINIDE ACETATE LEVELS IN NINE FASTED SUBJECTS FOLLOWING A TWO 100 mg ORAL DOSE OF FLECAINIDE ACETATE IN A CONVENTIONAL RELEASE TABLET AND IN A CAPSULE OF THE INVENTION

| | Capsule of the Invention | | Conventional Release | |
|---|---|---|---|---|
| Subject | Time to Peak (hr) | Peak Level (ng/mL) | Time to Peak (hr) | Peak Level (ng/mL) |
| 1 | 30 | 136 | 3 | 275 |
| 2 | 13 | 102 | 4 | 250 |
| 3 | 16 | 124 | 3 | 284 |
| 4 | 10 | 122 | 3 | 339 |
| 5 | 16 | 175 | 3 | 340 |
| 6 | 26 | 154 | 4 | 305 |
| 7 | 30 | 170 | 3 | 351 |
| 8 | 26 | 126 | 2 | 340 |
| 10 | 16 | 184 | 6 | 345 |
| Mean | 20[a] | 144[a] | 3.4 | 314 |
| S.D. | 8 | 28 | 1.1 | 37 |

[a]parameters were significantly different from the corresponding conventional release tablet parameters ($p \leq 0.05$)

What is claimed is:

1. A flecainide acetate controlled release pharmaceutical formulation comprising a film-coated bead which comprises a bead which is coated with a film-coat, wherein said bead comprises:
   (a) flecainide acetate present in an amount of about 20 to 80 percent by weight based on the total weight of said bead; and
   (b) microcrystalline cellulose present in an amount of about 80 to 20 percent by weight based on the total weight of said bead;

wherein said film-coat comprises:
   (a) a methacrylic acid/methyl methacrylate copolymer present in an amount of about 40 to 70 percent by weight based on the total weight of said film-coat;
   (b) a plasticizer present in an amount of about 5 to 20 percent by weight based on the total weight of said film-coat; and
   (c) a lubricant present in an amount of about 20 to 50 percent based on the weight of said film-coat; and wherein said film-coat is present in an amount of about 5 to 20 percent by weight based on the total weight of said film-coated bead.

2. A pharmaceutical formulation according to claim 1 wherein said bead comprises flecainide acetate present in an amount of about 70 to 80 percent by weight based on the total weight of said uncoated bead and microcrystallline cellulose present in an amount of about 20 to 30 percent by weight based on the total weight of said bead.

3. A pharmaceutical formulation according to claim 1 wherein said copolymer is USP/NF methacrylic acid/methyl methacrylate copolymer, Type B.

4. A pharmaceutical formulation according to claim 1 wherein said plasticizer is selected from the group consisting of polyethylene glycols, dibutyl phthalate and citric acid esters.

5. A pharmaceutical formulation according to claim 1 wherein said plasticizer is polyethylene glycol 400.

6. A pharmaceutical formulation according to claim 1 wherein said lubricant is talc.

7. A pharmaceutical formulation according to claim 1 wherein said film-coat is present in an amount of about 9 percent by weight based on the total weight of said film-coated bead.

8. A flecainide acetate controlled release formulation comprising a film-coated bead which comprises a bead which is coated with a film-coat wherein said bead comprises:
   (a) flecainide acetate present in an amount of about 75 percent by weight based on the total weight of said bead; and
   (b) microcrystalline cellulose present in an amount of about 25 percent by weight based on the total weight of said bead;
wherein said film-coat comprises:
   (a) USP/NF methacrylic acid/methyl methacrylate copolymer, Type B, present in an amount of about 57 percent by weight based on the total weight of said film-coat;
   (b) polyethylene glycol 400 present in an amount of about 10 percent by weight based on the total weight of said film-coat; and
   (c) talc present in an amount of about 33 percent by weight based on the total weight of said film-coat; and wherein said film-coat is present in an amount of about 9 percent by weight based on the total weight of said film-coated bead.

9. A flecainide acetate capsule comprising a hard gelatin capsule filled with a pharmaceutically effective amount of the pharmaceutical formulation according to claim 1, said capsule exhibiting controlled release of flecainide acetate in a human digestive tract.

10. A flecainide acetate capsule according to claim 9 wherein said capsule contains about 100 to 400 mg of flecainide acetate.

* * * * *